United States Patent [19]

Suzuki

[11] 3,975,449
[45] Aug. 17, 1976

[54] HYDROGENATION OF EPOXIDES TO PRIMARY ALCOHOLS

[75] Inventor: Shigeto Suzuki, San Francisco, Calif.

[73] Assignee: Chevron Research Company, San Francisco, Calif.

[22] Filed: Aug. 5, 1974

[21] Appl. No.: 494,572

[52] U.S. Cl................ 260/635 E; 260/45.85 T; 260/75 UA; 260/346.1 R; 260/348 R; 260/348.5 L; 260/410.6; 260/488 J; 260/632 B
[51] Int. Cl.² ........................................ C07C 29/00
[58] Field of Search.................. 260/635 E, 632 B

[56] References Cited
UNITED STATES PATENTS
3,028,431    4/1962    Webb ........................... 260/635 E OTHER PUBLICATIONS
Newman et al., "J. Am. Chem. Soc.", vol. 71 (1949), pp. 3362, 3363.

Primary Examiner—Joseph E. Evans
Attorney, Agent, or Firm—G. F. Magdeburger; John Stoner, Jr.; T. G. De Jonghe

[57] ABSTRACT

A process for producing a primary diol and/or triol from an epoxide which comprises contacting the epoxide with hydrogen gas and a solid catalyst comprising nickel or cobalt at a temperature between 20° and 200°C. and at a pressure sufficient to maintain liquid phase, and wherein the epoxide has the following formula:

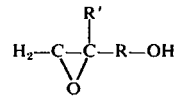

wherein R is an alkylene diradical of 1 to 5 carbon atoms and R' is a hydroxy alkyl having 1 to 5 carbon atoms or alkyl having 1 to 5 carbon atoms.

10 Claims, No Drawings

HYDROGENATION OF EPOXIDES TO PRIMARY ALCOHOLS

BACKGROUND OF THE INVENTION

The present invention relates to hydrogenation of epoxides to obtain alcohols.

The cleavage of epoxides to make new compounds containing a hydroxyl group is in general known in the art. See, for example, Morrison & Boyd, "Organic Chemistry," 2d Ed., at pp. 877–992.

A. Kotz and K. Righter in an article in J. Prakt. Chem. [2] 111, 373 (1925) disclose hydrogenation of an epoxide to obtain a secondary alcohol, as follows:

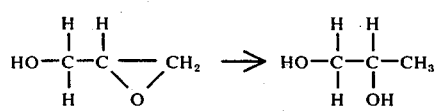

Park and Fuchs state in J. Org. Chem., January 1957, at page 93: "Only a few oxides with electron-withdrawing groups have been hydrogenated, and a secondary alcohol is always produced. Glycidol, epichlorohydrin, and butadiene dioxide are reduced to 1,2-propanediol, 1-chloro-2-propanol, and 2,3-butanediol, respectively, as the main product."

Searles and Butler in JACS, Vol. 76, p. 56 (1954), disclose reduction of 1-chloro-2,3-epoxy propane using hydrogen and a nickel catalyst. The product obtained is 1-chloro-2-propanol, that is, the epoxy group was reduced to result in the OH group being on the secondary rather than the primary carbon atom.

However, Newman, Underwood and Renoll in JACS, Vol. 71, p. 3362 (1949) disclose reduction of 1,2-epoxy decane using a nickel catalyst to obtain primary decane alcohol.

SUMMARY OF THE INVENTION

According to the present invention, a process is provided for producing a primary diol and/or triol from an epoxide, which process comprises contacting the epoxide with hydrogen gas and a solid catalyst comprising nickel or cobalt at a temperature between 20° and 200°C. and a pressure sufficient to maintain liquid phase, and wherein the epoxide has the following formula:

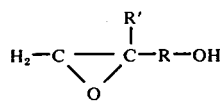

wherein R is an alkylene diradical of 1 to 5 carbon atoms and R' is a hydroxy alkyl having 1 to 5 carbon atoms or alkyl having 1 to 5 carbon atoms.

Among other factors, the present invention is based on my unexpected finding that in the process of the present invention the epoxide ring of an epoxidized alcohol is cleaved to give predominantly the corresponding hydroxy-containing primary alcohol. The dialcohols or trialcohols produced in the present invention have known utilities, including, for example, usefulness for making esters which in turn can be used as plasticizers in materials such as polyvinyl chloride.

The term "primary diol" is used herein to mean that the product has at least 2 hydroxyl groups in terminal positions, one of which hydroxyl groups is obtained from the epoxide ring.

Preferably the R' group of the epoxides used as feedstocks in the present invention in methyl, ethyl, propyl or 2'-hydroxyethyl. Preferably the alkylene group is a methylene, ethylene or propylene diradical. However, in broader embodiments of the present invention, the term "alkylene diradical" is used to include alkenylene diradicals and alkylidene diradicals, such as, respectively, $-C(CH_2)-$ and $-C(CH_3)-$. Particularly preferred epoxy feeds are 3,4-epoxy-3—methylbutanol, 2,3-epoxy-2-methylpropanol and 3,4-epoxy-3-(2'-hydroxyethyl)-butanol.

Preferred catalysts for use in the process of the present invention include Raney nickel, nickel on a solid inorganic refractory support, or Raney cobalt. Suitable solid inorganic refractory supports for supported catalysts include silica, alumina, magnesia, zirconia, titania, hafnia, and mixtures of silica-alumina such as in a kieselguhr support. A particularly preferred catalyst for use in the process of the present invention is Raney nickel.

Preferred reaction conditions include a temperature between about 50°and 250°C., more preferably 80°and 200°C., and a hydrogen pressure between about 100 and 10,000 psig, preferably 500 to 5000 psig.

According to a preferred embodiment of the present invention, a process is provided for producing 2-methyl-1,4-butanediol from 3,4-epoxy-3-methylbutanol, which process comprises contacting the epoxide with hydrogen gas and a solid catalyst comprising nickel or cobalt, preferably Raney nickel, at a temperature between about 80° and 190°C. and at a pressure sufficient to maintain the epoxide feed and alcohol product in liquid phase.

Reference to the catalyst as a nickel or cobalt catalyst is meant to include the metal in the compound form as well as the elemental form, for example as nickel oxide or sulfide or as a nickel hydride, or as the reduced elemental nickel or as mixtures of the foregoing. Suitable amounts of catalysts for use in the process of the present invention range from 10 to 60 weight percent metal catalyst, based on epoxide. Preferably the catalyst is utilized in 30 to 50 weight percent on the same basis.

Solvents

The hydrogenation reaction of the present invention is preferably carried out in the presence of a solvent. The solvent is utilized primarily to prevent polymerization of the epoxide starting material; thus hydrogenation in the absence of a solvent usually results in a low yield of the desired polyhydroxy product. The preferred solvents are polar organic liquids, preferably having one or more hydroxyl groups. Examples of satisfactory solvents include the low-molecular-weight alcohols such as methanol, ethanol, propanol and butanol; the low-molecular-weight dihydroxy compounds such as ethylene glycol, diethylene glycol, 1,3-propanediol, 2-methyl-1,3-pentanediol, and 2-methyl-1,4-pentanediol; low-molecular- weight trihydroxy compounds such as glycerol; and nonhydroxylic solvents such as N-methyl-pyrrolidone, dimethylformamide and hexamethylphosphorotriamide. The preferred solvents are methanol and ethanol.

The quantity of solvent employed in the hydrogenation reaction of the present invention may cover a wide range of concentrations. Preferably the epoxide is kept at a rather low concentration, usually in the range of 5 to 50 weight percent, based on solvent. At lower concentrations, although the hydrogenation proceeds satisfactorily, the separation of product and recovery of solvent becomes more expensive. At higher concentrations, polymerization usually becomes a serious side reaction.

Starting Material

The epoxy alcohols needed as feedstock for the present process are preferably prepared by epoxidizing the corresponding unsaturated alcohol. Epoxidation is readily accomplished by reacting an unsaturated alcohol with a peroxidic material such as hydrogen peroxide, peracetic acid, perbenzoic acid, etc. Such processes are well known in the art (see, for example, "Organic Synthesis," Collective Vol. I, 2d Ed., Wiley, New York, 1949, page 949). Unsaturated alcohols are available from a variety of sources; however, a convenient method of preparation is via the reaction of an olefin and formaldehyde. For example, isobutene-formaldehyde reaction yields 3-methyl-3-buten-1-ol; further reaction of this compound with formaldehyde yields about 50% of 3-methylene-1,5-pentanediol. Both of these compounds may be epoxidized and then hydrogenated by the process disclosed herein to produce 2-methyl-1,3-propanediol and 3-methylol-1,5-pentanediol, respectively. Another useful unsaturated alcohol for epoxidation and subsequent hydrogenation is 2,3-dimethyl-3-butenol, which gives 2,3-dimethyl-1,4-butanediol as the final product.

Other useful epoxy alcohols for the present process include:
2,3-epoxy-2-ethylpropanol,
3,4-epoxy-3-methylbutanol,
4,5-epoxy-4-ethylpentanol,
3,4-epoxy-3-(2'-hydroxyethyl)-butanol,
4,5-epoxy-4-(2'-hydroxyethyl)-pentanol,
6,7-epoxy-6-methyl-heptanol,
2,3-epoxy-2-pentylpropanol,
2,3-epoxy-2-(2'-methylpropyl)-propanol,
6,7-epoxy-6-(2'-methyl-4'-hydroxybutyl)-heptanol,
4,5-epoxy-2,3,4-trimethylpentanol,
4,5-epoxy-3,3,4-trimethylpentanol,
5,6-epoxy-3-ethyl-4,5-dimethylhexanol,
4,5-epoxy-2,4-dimethylpentanol, etc.

Processing

The hydrogenation process of the present invention can be carried out by either a batch or a continuous procedure. In a batch operation, preferably the epoxy alcohol, solvent and catalyst are charged to an appropriate reactor, such as an autoclave or other pressure vessel. Hydrogen gas is charged to the reactor and the contents are heated to the desired temperature. The reaction mixture is stirred or shaken to maintain good contact of the reactants. Preferably hydrogen is continuously added, as from an accumulator, to maintain a constant pressure throughout the run; but alternatively, excess hydrogen can be added initially and the reaction run until no more pressure drop occurs.

In continuous processing, preferably the epoxy alcohol dissolved in a solvent is continuously mixed with catalyst and charged to a heated and baffled tubular reactor wherein hydrogen gas is maintained at the desired pressure. Hydrogen can be introduced at several inlets located along the length of the reactor.

In either processing scheme, the liquid reaction product mixture is worked up by first removing the catalyst by filtration or centrifugation. (A filter aid may be necessary at this stage). Then the solvent is removed by distillation to give a crude bottoms product which is satisfactory for many applications, e.g., for esterification. However, the crude may also be purified by distillation or in some cases by crystallization.

Utility

The products produced by the process of the present invention are useful for many applications. The primary diols are particularly preferred in the preparation of unsaturated polyesters by reaction with maleic or fumaric acid. Another application is in the preparation of high-molecular-weight diesters, such as by reaction with stearic acid, caprylic acid, and arachidic acid, etc. These diesters are useful plasticizers. Furthermore, the low-molecular-weight diols are useful solvents. The triol products resulting from hydrogenation of an epoxy diol ($R'=a$ hydroxy alkyl group) are particularly preferred for conversion to high-molecular-weight triesters for use as plasticizers.

EXAMPLES

Example 1

Preparation of 2-methyl-1,4-butanediol a. A microbomb of 15-ml capacity was charged with 0.5 g (0.0049 mol) of 3,4-epoxy-3-methyl-1-butanol, 0.2 g of Raney nickel, and 2 ml each of water and ethanol. The bomb was charged with hydrogen and was then heated and shaken at 150°C. while the pressure was maintained at a constant 1500 psig. After 1 hour, the reactor was cooled and the contents were analyzed by vapor phase chromatography. The reaction product contained 83.5% 2-methyl-1,4-butanediol, 14.1% 3-methylbutanol, and 2.4% 3-methyl-1,3-butanediol. (Percentages are by weight unless otherwise indicated). There was no evidence of any 2-methyl-1,2,4-butanetriol, as would result from hydration of the epoxide ring.

b. A similar experiment, carried out in 5 ml of anhydrous ethanol, produced 75% 2-methyl-1,4-butanediol, 11.6% 3-methylbutanol, and 12.4% 3-methyl-1,3-butanediol.

c. Another experiment was carried out as in Example 1(a), except that the ethanol was replaced by an equal weight of methanol, and the reaction temperature was held at 125°C. In this case, the yields were 67% 2-methyl-1,4-butanediol, 13% 3-methylbutanol, 1% 3-methyl-1,3-butanediol and 13% 3-methyl-tetrahydrofuran.

d. A final experiment was carried out as in Example 1(a), except that the solvent was 4 ml of water. In this case, the yield was 60% 2-methyl-1,4-butanediol, 5% 3-methylbutanol, and 34% 2-methyl-1,2,4-butanetriol.

These results indicate that although good yields of the desired diol are obtainable in water, a preferred solvent is a mixture of low-molecular-weight alcohol and water.

EXAMPLE 2

Preparation of 2-methyl-1,3-propanediol a. This example was carried out in the same way as Example 1(a), except that the charged consisted of 0.5 g (0.0059) mol) of 2,3-epoxy-2-methylpropanol, and the reaction was continued for 4 hours. At the end of this time, the product was found to contain 82.1% 2-methyl-1,3-propanediol (2-MPD), 6% 2-methyl-propanol (2-MP), and 11.2% 1,1-dimethyl-1,2-ethanediol (DMED). There was no trace of 2-methyl-1,2,3,-propanetriol.

b. Example 2(a) was repeated, using 2-propanol as a cosolvent in place of ethanol. The results were essentially the same, i.e., 78% 2-MPD, 6% 2-MP, and 16% DMED.

EXAMPLE 3

Effect of Solvent on Yield of 2-methyl-1,3-propanediol

A series of hydrogenations was carried out in the same way as Example 1(a), but utilizing 2,3-epoxy-2-methyl-propanol as the feedstock and different solvent systems. The results are tabulated below:

| Ex. No. | Solvent Nature | Quantity (ml) | Product Distribution, % | | |
|---|---|---|---|---|---|
| | | | 2-MPD | 2-MP | DMED |
| 3(a) | ethanol | 5 | 56.1 | 6.4 | 37.6 |
| 3(b) | ethanol, water | 2,4 | 68.9 | 8.1 | 8.3 |
| 3(c) | n-butanol | 5 | 63.4 | 9.8 | 26.8 |
| 3(d) | i-butanol | 5 | 65.0 | — | 35.0 |
| 3(e) | i-butanol, water | 2,2 | 84.0 | — | 11.3 |
| 3(f) | t-butanol | 5 | 55.0 | 5.4 | 39.6 |
| 3(g) | t-butanol, water | 2,2 | 76.4 | 8.0 | 15.6 |

These examples show that nearly equivalent results are obtained with any of the low-molecular-weight alcohols and that mixtures of alcohol and water are superior to anhydrous alcohols as a solvent. Surprisingly, the presence of water in the solvent increases the amount of the desired diprimary alcohol at the expense of the secondary hydroxy-containing alcohol (DMED).

Another series of runs was carried out as above, except that the reaction time was 4 hours. The results are tabulated below:

| Ex. No. | Solvent Nature | Quantity (ml) | Product Distribution, % | | |
|---|---|---|---|---|---|
| | | | 2-MPD | 2-MP | DMED |
| 3(h) | water | 5 | 68.0 | 12.6 | 9.0 |
| 3(i) | diethylene glycol | 4 | 63.5 | 15.6 | 11.7 |
| 3(j) | methanol | 4 | 65.8 | 12.4 | 21.9 |
| 3(k) | methanol, water | 2,2 | 81.1 | 10.9 | 8.0 |
| 3(l) | N-methylpyrrolidone | 4 | 43.1 | 3.5 | 35.3 |

This series confirms the conclusions given above and also shows that low-molecular-weight glycols are satisfactory solvents. Run 3(b) shows that polar nonhydroxylic organic liquids can also function as solvents; however, low-molecular-weight alcohol-water combinations are preferred.

EXAMPLE 4

Effect of Catalyst on Yield of 2-methyl-1,3-propanediol

The apparatus of Example 1 was charged with 0.5 g (0.0057 mol) of 2,3-epoxy-2-methylpropanol. The reactor was also charged with a solvent and a catalyst, as indicated below. The apparatus was charged with hydrogen, which was maintained at a constant pressure of 1500 psig throughout the run. The reaction was continued for 4 hours at 150°C. The results are tabulated below:

| Example | Catalyst Species | Quantity (grams) | Solvent Nature | Quantity (ml) | Product Distribution, % | | |
|---|---|---|---|---|---|---|---|
| | | | | | 2-MPD | 2-MP | DMED |
| 3(h) | Raney nickel | 0.2 | Water | 5 | 68 | 12.6 | 9 |
| 4(a) | Raney cobalt | 0.2 | Water | 5 | 39 | 9 | 2 |
| 4(b) | Raney cobalt | 0.2 | Ethanol | 5 | 54 | 44 | <1 |
| 4(c) | 60% Ni on kieselguhr | 0.3 | Ethanol, water | 2,2 | 66.3 | 7.6 | 23.8 |
| 4(d) | 5% Ru on carbon | 0.3 | Ethanol | 5 | 39.0 | 12.9 | 0.8 |
| 4(e) | 5% Ru on carbon | 0.3 | Ethanol, water | 2,2 | 26.6 | 10.3 | <1 |
| 4(f)[1] | 5% Pd on carbon | 1.0 | Ethanol | 4 | <1 | 6 | 94 |
| 4(g)[1] | 5% Pd on carbon | 1.0 | Acetic Acid | 4 | 10 | 3 | 82 |
| 4(h) | Cu chromite, Ba oxide | 0.2 | Water | 5 | 5.5 | 4.9 | <1 |
| 4(i) | Platinum oxide | 0.05 | Water | 4 | 16.6 | 4.5 | 3.8 |
| 4(j) | Platinum oxide | 0.05 | Acetic Acid | 4 | 20.0 | 26.6 | 7.2 |

[1]Reaction continued for 2 hours at 25°C.

This series of experiments shows that nickel on kieselguhr and Raney cobalt are satisfactory catalysts for the reduction of epoxy alcohols. However, Raney nickel is preferred.

EXAMPLE 5

Effect of Time and Temperature on Yield of 2-methyl-1,3-propanediol

A series of experiments was carried out in the apparatus of Example 1. The charge consisted of 0.5 g (0.0057 mol) of 2,3-epoxy-2-methylpropanol, 0.2 g of Raney cobalt, and 5 ml of ethanol. The reactor was charged with 1500 psig of hydrogen, which was maintained constant throughout the run. The time and temperature of reaction and the results are tabulated below:

| Ex. No. | Reaction Conditions | | Product Distribution, % | | |
|---|---|---|---|---|---|
| | Time, Hrs. | T.,°C | 2-MPD | 2-MP | DMED |
| 5(a) | 1 | 150 | 57.6 | 40.0 | 0.6 |
| 5(b) | 4 | 120 | 59.4 | 37.6 | 1.3 |
| 5(c) | 2 | 80 | 60.7 | 37.0 | 1.2 |
| 5(d) | 2 | 50 | 15.4 | 15.1 | <1 |
| 5(e) | 2 | 25 | 0 | 0 | 0 |
| 4(b) | 4 | 150 | 54 | 44 | <1 |

These results show that under these conditions the hydrogenation is complete after 2 hours at 80°C, but has not begun after 2 hours at 25°C. They also show that longer reaction times or higher temperatures may cause some loss of product to 2-methylpropanol.

Another series of experiments was carried out as described above, except that the catalyst was 0.2 g of Raney nickel. The solvent was composed of 2 ml each of water and ethanol. The results were as follows:

| Ex. No. | Conditions Time, Hrs. | T.,°C | 2-MPD | Product Distribution, % 2-MP | DMED |
|---|---|---|---|---|---|
| 5(f) | 4 | 100 | 64.9 | 6.6 | 18.9 |
| 5(g) | ½ | 180 | 72.9 | 13.2 | 7.4 |
| 3(h)[1] | 1 | 150 | 68.9 | 8.1 | 8.3 |

[1] The solvent consisted of 2 ml ethanol and 4 ml of water.

EXAMPLE 6

Hydrogenation of Glycidol

In the same apparatus and following the same procedure as before, 0.5 g (0.0068 mol) of glycidol (2,3-epoxy-propanol) was hydrogenated over 0.2 g of Raney nickel at 1500 psig of hydrogen pressure. The solvent was composed of 2 ml each of ethanol and water. The time and temperature of the reactions and the results are as follows:

| Ex. No. | Conditions Time, Hrs. | T.,°C | 1,3-PD[1] | Product Distribution, % 1,2-PD[2] | Other |
|---|---|---|---|---|---|
| 6(a) | 2 | 25 | <1 | 22.5 | 77[3] |
| 6(b) | 2 | 100 | 3.4 | 90.5 | 6(?) |
| 6(c) | 4 | 150 | 13 | 73 | 14(?) |

[1] 1,3-PD: 1,3-propanediol
[2] 1,2-PD: 1,2-propanediol
[3] Unreacted glycidol starting material These results confirm the teaching of the prior art, namely, hydrogenation of an epoxy group usually gives mainly a secondary hydroxyl group in preference to a primary hydroxyl group.

EXAMPLE 7

Preparation of 3-methylol-1,5-pentanediol

A 500-ml flask equipped with a thermometer, reflux condenser, dropping funnel and a stirrer was charged with 86 g (0.74 mol) of 3-methylene-1,5-pentanediol, 100 ml of benzene, and 0.9 g of vanadyl diacetylacetonate. This mixture was stirred while 79.3 g (0.81 mol) of t-butylhydroperoxide was added dropwise, at a rate sufficient to maintain a temperature of about 80°C. After all of the hydroperoxide was added (about 30 minutes), the mixture was refluxed for 4 hours. Then the reaction mixture was concentrated by evaporation in a rotating flask at about 40°C. under 110 mm Hg pressure. The concentrated product, crude 3,4-epoxy-3-(2'-hydroxyethyl)-butanol, weighed 129 g. A vapor phase chromatographic analysis showed essentially 100% conversion of t-butylhydroperoxide.

The crude epoxide from the above (128.8 g) was charged to a 1-liter stirred autoclave along with 150 ml of ethanol, 150 ml of water, and 30 g of Raney nickel. The autoclave was then charged with 1620 psig of hydrogen at 25°C. Stirring was started and the autoclave was heated to 150°C. When the hydrogen pressure reached 1300 psig at this temperature, the autoclave was repressured with hydrogen to 1620 psig. The hydrogenation reaction was continued for 3 ½ hours. After cooling to room temperature, the reaction mixture was filtered and concentrated to 91.5 g by heating at 40°C. under 110 mm Hg pressure. Analysis by vapor phase chromatography showed 53% 3-methylol-1,5-pentanediol and 38% 3-methyl-1,5-pentanediol.

Two additional hydrogenations were carried out in essentially the same way on 180-g epoxy charges. The crude products of all three runs were combined and 391.7 g of it was charged to a 10" zig-zag column. Distillation was carried out under a reduced pressure to remove 67 g of material boiling below 108°C. under 0.5 mm Hg pressure. Then the pressure was further reduced and an intermediate fraction, having a boiling range of 93° to 193°C. at 0.07 mm Hg pressure, was obtained. Then the product was distilled overhead at a boiling point of 193°–197°C. at 0.07 mm Hg pressure. Recovery of distilled 3-methylol-1,5-pentanediol was 139 g. The presence of a substantial quantity of 3-methyl-1,5-pentanediol in the crude product indicated incomplete epoxidation of 3-methylene-1,5-pentanediol.

A portion of the distilled 3-methylol-1,5-pentanediol was esterified with n-hexanoic acid. The resulting triester (40 parts by weight), polyvinyl chloride (60 parts) and a barium-cadmium soap mixture (1 part) were mixed on a rubber mill until homogenous. The resulting product was soft and flexible, thus illustrating the usefulness of the 3-methylol-1,5-pentanediol as a plasticizer.

What is claimed is:

1. A process for producing a primary alcohol as the main product from an epoxide which comprises contacting the epoxide with hydrogen gas and a solid catalyst comprising nickel or cobalt at a temperature between 20° and 200°C. and a pressure sufficient to maintain liquid phase and wherein the epoxide has the following formula:

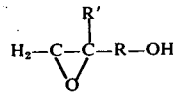

wherein R is an alkylene diradical of 1 to 5 carbon atoms and R' is a hydroxy alkyl or alkyl having 1 to 5 carbon atoms. wherein the epoxide contacting is carried out in the presence of a solvent comprising a low molecular weight alcohol and water, and wherein the nickel or cobalt of the solid catalyst are in the elemental form or are the sulfide, oxide or hydride, thereby producing primary alcohol from the epoxide as the main product of the epoxide hydrogenation.

2. A process in accordance with claim 1 wherein R' is methyl, ethyl, propyl or beta-hydroxyethyl.

3. A process in accordance with claim 1 wherein the catalyst is Raney nickel, nickel on a solid inorganic refractory support or Raney cobalt.

4. A process in accordance with claim 3 wherein the catalyst is Raney nickel.

5. A process in accordance with claim 1 wherein the temperature is between 80° and 200°C.

6. A process in accordance with claim 1 wherein the epoxide is 3,4-epoxy-3-methylbutanol.

7. A process in accordance with claim 1 wherein the alcohol is methanol, ethanol, i-butanol, or t-butanol.

8. A process in accordance with claim 5 wherein the feed is 3,4-epoxy-3-methylbutanol and the primary alcohol product is 2-methyl-1,4-butanediol.

9. A process in accordance with claim 5 wherein the feed is 2,3-epoxy-methylpropanol and the primary alcohol product is 2-methyl-1,3-propanediol.

10. A process in accordance with claim 5 wherein the feed is 3,4-epoxy-3-(2'-hydroxyethyl)-butanol and the primary alcohol is 3-methylol-1,5-pentanediol.

* * * * *